(12) United States Patent
Kazerooni et al.

(10) Patent No.: US 11,684,536 B2
(45) Date of Patent: Jun. 27, 2023

(54) FALL PREVENTION APPARATUS

(71) Applicant: The Regents of the University of California, Oakland, CA (US)

(72) Inventors: Homayoon Kazerooni, Berkeley, CA (US); Mimi Parker, Berkeley, CA (US); Lace Co Ting Keh, La Crescenta, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/189,809

(22) Filed: Nov. 13, 2018

(65) Prior Publication Data
US 2019/0142683 A1 May 16, 2019

Related U.S. Application Data

(60) Provisional application No. 62/585,438, filed on Nov. 13, 2017.

(51) Int. Cl.
*A61H 3/00* (2006.01)
*A61F 2/70* (2006.01)
(Continued)

(52) U.S. Cl.
CPC .............. *A61H 3/008* (2013.01); *A61F 2/70* (2013.01); *A61H 3/00* (2013.01); *A61H 3/04* (2013.01);
(Continued)

(58) Field of Classification Search
CPC . A61H 3/00; A61H 3/008; A61H 3/02; A61H 3/04; A61H 3/06; A61H 2003/007;
(Continued)

(56) References Cited

U.S. PATENT DOCUMENTS 4,245,659 A * 1/1981 Shofner .................... A61H 3/02
135/68
6,578,594 B1 6/2003 Bowen et al.
(Continued)

FOREIGN PATENT DOCUMENTS

KR 20120131732 A 12/2012
WO 2019094961 A1 5/2019

OTHER PUBLICATIONS

"Int'l Application Serial No. PCT/US18/60811, Int'l Search Report and Written Opinion dated Feb. 27, 2019", 9 pgs.

*Primary Examiner* — Michelle J Lee
(74) *Attorney, Agent, or Firm* — Sterne, Kessler, Goldstein & Fox P.L.L.C.

(57) ABSTRACT

A fall prevention device configured to be coupled to a person and comprising a mechanical torso configured to be coupled to the person's torso and a mechanical structure configurable to be coupled to the mechanical torso from its first end. The mechanical structure and mechanical torso resist forces at least along one direction to maintain their posture relative to each other. In operation the second end of the mechanical structure is positioned behind the person and substantially close to the ground. When the second end of the mechanical structure contacts the ground, contact points of legs of the person on the ground and contact points of the second end of the mechanical structure outline a multi-sided polygon on the ground. If the vertical projection of the center of gravity of the person to the ground intersects the ground within the multi-sided polygon, the person and fall prevention device remain stable.

29 Claims, 20 Drawing Sheets

(51) Int. Cl.
 *A61H 3/04* (2006.01)
 *B25J 9/00* (2006.01)

(52) U.S. Cl.
 CPC ....... *B25J 9/0006* (2013.01); *A61F 2002/701* (2013.01); *A61F 2002/704* (2013.01); *A61H 2003/007* (2013.01); *A61H 2201/0161* (2013.01); *A61H 2201/0192* (2013.01); *A61H 2201/163* (2013.01); *A61H 2201/165* (2013.01); *A61H 2201/1616* (2013.01); *A61H 2201/1642* (2013.01); *A61H 2201/1652* (2013.01)

(58) Field of Classification Search
 CPC .... A61H 2003/0205; A61H 2003/0216; A61H 2003/0294; A61H 2201/00; A61H 2201/01; A61H 2201/0161; A61H 2201/0192; A61H 2201/16; A61H 2201/1614–1633; A61H 2201/164; A61H 2201/1642; A61H 2201/165; A61H 2201/1652; A47D 13/04; A47D 13/046; B25J 9/006; B25J 9/00; B25J 9/0006; A61F 2/68; A61F 2/70–72
 See application file for complete search history.

(56) References Cited

U.S. PATENT DOCUMENTS

| | | | |
|---|---|---|---|
| 9,393,173 B1 | 7/2016 | Meza | |
| 10,596,012 B2 * | 3/2020 | Hummelshøj | A61F 2/70 |
| 10,835,443 B2 * | 11/2020 | Tsai | A61F 2/70 |
| 2006/0064047 A1 * | 3/2006 | Shimada | A61F 5/0102 602/26 |
| 2012/0316476 A1 * | 12/2012 | Shimizu | A61H 3/00 601/35 |
| 2014/0196757 A1 * | 7/2014 | Goffer | A61H 1/0262 135/66 |
| 2014/0358053 A1 * | 12/2014 | Triolo | B25J 9/0006 602/19 |
| 2016/0038371 A1 * | 2/2016 | Sandler | A61H 3/02 602/19 |
| 2018/0257217 A1 * | 9/2018 | Johnson | B25J 19/0012 |

* cited by examiner

FALL PREVENTION APPARATUS

CROSS-REFERENCE TO RELATED APPLICATIONS

This application claims the benefit under 35 U.S.C. § 119(e) of U.S. Provisional Patent Application No. 62/585,438, filed on Nov. 13, 2017, which is incorporated herein by reference in its entirety for all purposes.

STATEMENT REGARDING FEDERALLY SPONSORED RESEARCH OR DEVELOPMENT

This invention was made with government support under Contract No. 1545106 awarded by the National Science Foundation. The government has certain rights in the invention.

TECHNICAL FIELD

This disclosure relates generally to preventing backward fall in individuals with risk of falling or individuals wearing exoskeletons. Embodiments disclosed herein describe an apparatus coupled to a person with risk of falling or wearing exoskeletons, which provides posterior stability while performing various tasks ranging from locomotion to maintaining stationary positions.

BACKGROUND

An exoskeleton is a mechanism that can be externally worn or coupled to an individual in order to enhance his/her endurance, strength, or ability. The particular type of exoskeleton considered is used by an individual who has limited movements in her/his lower extremities. Currently several medical exoskeleton systems are sold by various manufacturers. The current exoskeletons, under the FDA's limited approval, are required to be operated under a companion supervision or in a controlled environment. These exoskeletons are employed while they are hung to overhead cranes, or at least one other person (e. g., physical therapist) closely follows the user to catch the user before fall. One must bear in mind that the exoskeleton users have already been injured or have very limited to no mobility on their own. If a person using an exoskeleton falls, additional (and sometimes irreversible) injuries may occur that lead to further disability, since users typically have bone density loss and osteoporosis, which increase the risk of fracture. Even if there is no injury after falling, it is unclear whether an exoskeleton user with limited mobility, wearing an exoskeleton, could stand up again without aid from another person.

A support mechanism configured to be coupled to an exoskeleton is disclosed in Pat. Pub. No. US 2003/0093021 A1 by Amit Goffer titled Gait-Locomotor Apparatus. This support mechanism is configured to be two side crutches coupled to an exoskeleton and is located at the body sides. In some embodiments, lateral stability is achieved through the use of the support mechanism. The support mechanism is also proposed to improve backward and forward stability by controlling the location of the crutches either by the user or by actuators. Two side crutches are coupled to a handle that can be used by the wearer to manipulate the crutches. The two side crutches are retractable so as to facilitate height adjustments. In some embodiments, the crutches may comprise of two telescopically connected members that allow this feature.

An automated fall prevention mechanism is configured to be coupled to an exoskeleton or directly to user has been disclosed in U.S. Pat. No. US 2014/0005577 A1 by Amit Goffer titled Airbag for Exoskeleton Device. The proposed automated fall prevention mechanism is configured to be one or a plurality of airbags may be configured to deploy on the back and/or around the area of the waist of the user. The proposed automated fall prevention mechanism is coupled to a plurality of actuators and sensors that deploy the airbag when disequilibrium is sensed. The airbag may be manually deployed by the user.

A support mechanism configured to be coupled to gait devices has been disclosed in U.S. Patent Application Pub. No. US 2014/0196757 A1 by Amit Goffer titled Gait Device with a Crutch. The proposed support mechanism is configured to be crutches or a crutch like device. The support mechanism is proposed to be a locomotion facilitator and a locomotion modifier. It may include mechanical and/or electrical mechanisms to modify locomotion over a surface in order to enhance locomotion of the user.

Furthermore, safety measure of current exoskeletons is summarized and highlighted in "Risk Management and Regulations for Lower Limb Medical Exoskeletons: A Review", published in Medical Devices vol. 10, pp. 89-107. An approach significant to the topic is the mechanism of 'graceful falling', which activates the graceful collapse of the exoskeleton into a sitting or kneeling position without harming the user in the in which the functionality of the exoskeleton is compromised. A similar study was done by the University of British Columbia Engineering Physics team under Dr. Jaimieb Borisoff, Masha Khalili, and Dr. Machiel Van Der Loos in 2016, titled "Inverted Triple Link Pendulum Model for Development of a Human Exoskeleton Safe-Fall Algorithm" and mentioned in Khalili's thesis "Developing Control Strategies to Mitigate Injury After Falling Backward with a Lower Limb Exoskeleton". The project seeks to determine the trajectory of a fall and minimize the impact velocity of the user by 'rapid knee flexion'.

DESCRIPTION OF EMBODIMENTS

In various embodiments, stabilizing an exoskeleton and its wearer (i.e., preventing fall or reducing the risk of fall) is an engineering task addressed by embodiments disclosed herein. Accordingly, embodiments disclosed herein provide a mechanism that reduces the risk of fall of a person using an exoskeleton. Embodiments disclosed herein can also be used by a person who is not wearing an exoskeleton but is at the risk of falling.

Accordingly, various embodiments described herein provide solutions by adding a posterior support mechanism to a lower extremity exoskeleton, or a supportive gait device in order to prevent instability. The device can also be used without any exoskeleton. The proposed device allows for the adjustment in the length of the supports. This allows for adjustment for the user's height, as well as the adjustment of the extent or maximum degree of incline experienced when in the unstable position.

Figure 1:
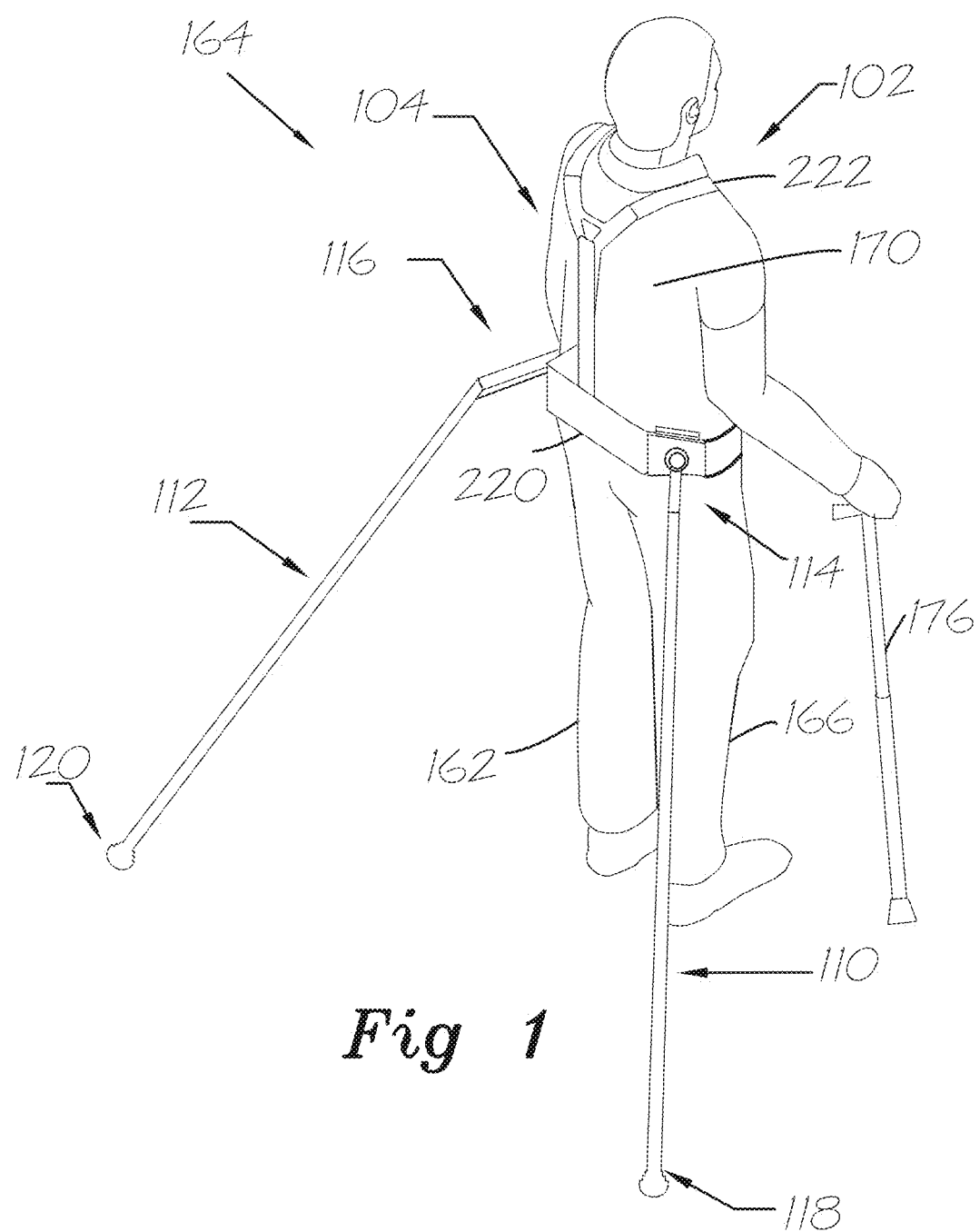
FIG. 1 depicts an embodiment of fall prevention device with two mechanical structures.
Figure 2:
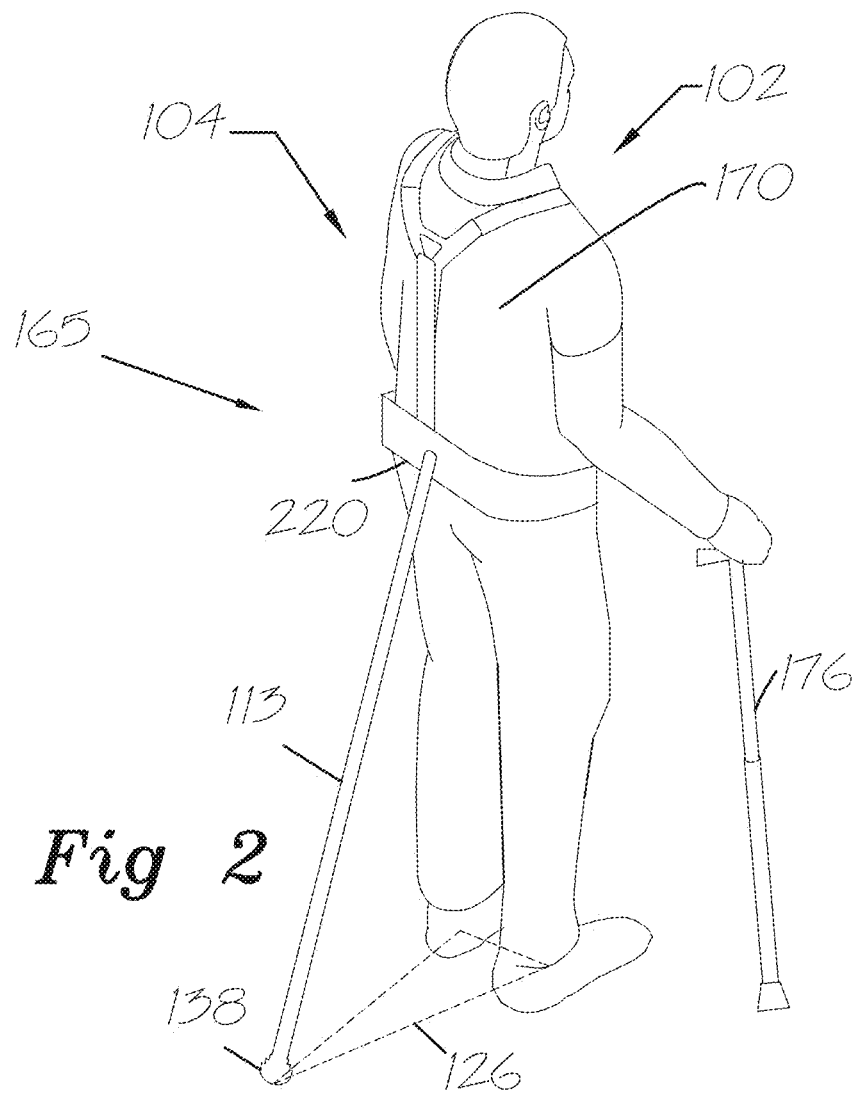
FIG. 2 depicts an embodiment of fall prevention device with one mechanical structure.

FIG. 1 shows an embodiment of fall prevention device 164. Fall prevention device 164 is configured to be coupled to person (also referred to as wearer or user) 102. Fall prevention device 164 comprises: a mechanical torso 104 which is configured to be coupled to the torso 170 of person 102, and at least one mechanical structure 110. FIG. 1 shows an embodiment with two mechanical structures 110 and 112. Other embodiments with one mechanical structure 113 is shown in FIG. 2. For brevity, we describe using two mechanical structures 110 and 112; however, all characteristics outlined below are equally applicable to fall prevention device 165 with one mechanical structure 113 as shown in FIG. 2. Mechanical structures 110 and 112 are configurable to be securely coupled to mechanical torso 104 from its first ends 116 and 114. The coupling of mechanical structure 110 and mechanical torso 104 is such that they resist forces to maintain their posture relative to each other. In other words, mechanical structure 110 and mechanical torso 104 do not rotate or move easily and effortlessly relative to each other. The same is true for coupling of mechanical structure 112 and mechanical torso 104; the coupling of mechanical structure 112 and mechanical torso 104 is such that they resist forces, at least along one direction, in order to maintain their posture relative to each other. Mechanical torso 104 is configured to be coupled to torso 170 of person 102. In some embodiments, mechanical torso 104 comprises a belt structure 220 configurable to be coupled to torso 170 of person 102 through straps and belts. The posterior of belt structure 220 which is located behind the person is a rigid structure capable of coupling to mechanical structures 110 and 112. In some embodiments, mechanical torso 104 comprises shoulder straps 222 for coupling mechanical torso 104 to torso 170 of person 102.

Figure 3:
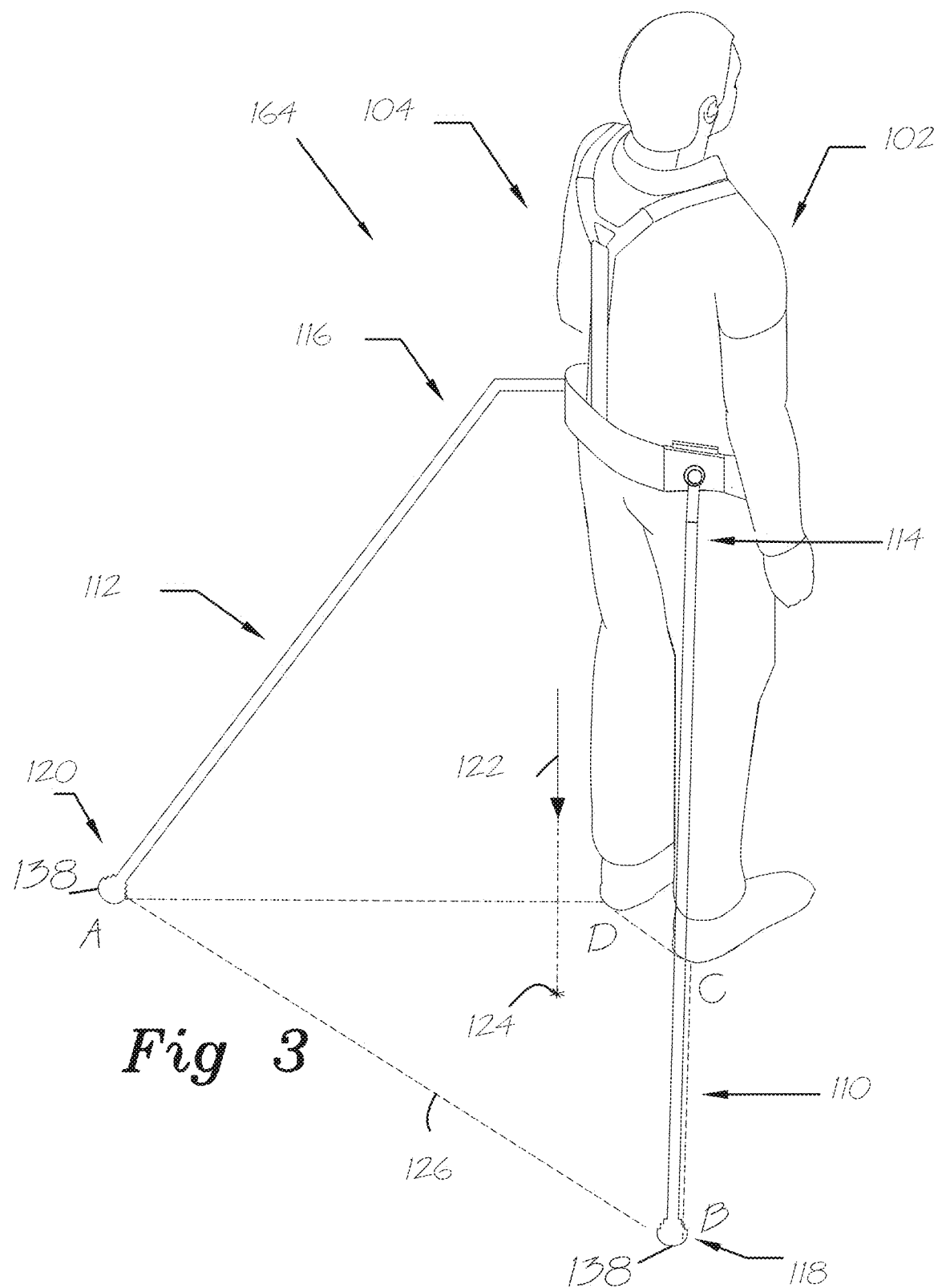
FIG. 3 depicts an embodiment of fall prevention device with two mechanical structures forming a four-sided polygon in conjunction with the human legs.

Operation of the fall prevention device 164 is now described with the help of FIG. 3. In the embodiment of FIG. 3, both mechanical structures 110 and 112 are employed. In operation, as shown in FIG. 3, when the second ends 118 and 120 of mechanical structures 110 and 112 contact the ground (represented by B and A, respectively), the contact points of the legs of the wearer on the ground (represented by C and D), and the contact points of the second ends 118 or 120 of mechanical structures 110 and 112 on the ground (shown by B and A, respectively) outline a multi-sided polygon 126 on the ground. When a vertical projection, such as vertical gravitational line 122 (also referred to herein as a vertical gravity line), of the center of gravity of person 102 to the ground intersects the ground within multi-sided polygon 126 at point 124, person 102 will not fall backward. Fall prevention device 164 reduces the risk of backward and sideway fall of person 102. The rigidity of coupling of mechanical structures 110 and 112 to mechanical torso 104 is important for stability of person 102 when the fall prevention device is coupled to the person. If mechanical structures 110 and 112 move or rotate relative to mechanical torso 104 (for example, if revolute joints are used between mechanical structures 110 and 112, and mechanical torso 104), then person 102 will fall. The rigidity of coupling of mechanical structures 110 and 112 to mechanical torso 104 ensures that the assembly formed by two mechanical structures 110 and 112 and wearer or person 102's body will remain upright and stable as long as the wearer or person 102's joints (e.g., hip, knee or ankle) are capable of providing torques. Person 102 may or may not hold onto cane 176 or crutches (shown in FIG. 1). Crutches or cane 176 generally reduce the risk of forward fall.

In some embodiments, the coupling of mechanical structures 110 and 112 to mechanical torso 104 comprises some structural compliancy due to the materials used in mechanical structures 110 and 112 or mechanical torso 104. This structural compliancy allows mechanical structures 110 and 112 to resist forces to preserve their posture relative to mechanical torso 104 at least along one direction so the person does not fall. FIG. 2 shows an embodiment where only one mechanical structure has been employed to perform the intended function. In the embodiment of FIG. 2, multi-sided polygon 126 is a triangle. The larger multi-sided polygon 126 is, the more stable the person will be. It can be noted that the fall prevention device 164 of embodiment in FIG. 3 provides more stability range for person 102 than the fall prevention 164 device of embodiment in FIG. 2 does.

FIG. 2 and FIG. 3 show an embodiment of fall prevention device 164 wherein second ends 118 and 120 of mechanical structures 110 and 112 each has an attachment 138 providing a rubbery grip or adding traction to the ground.

Figure 4:
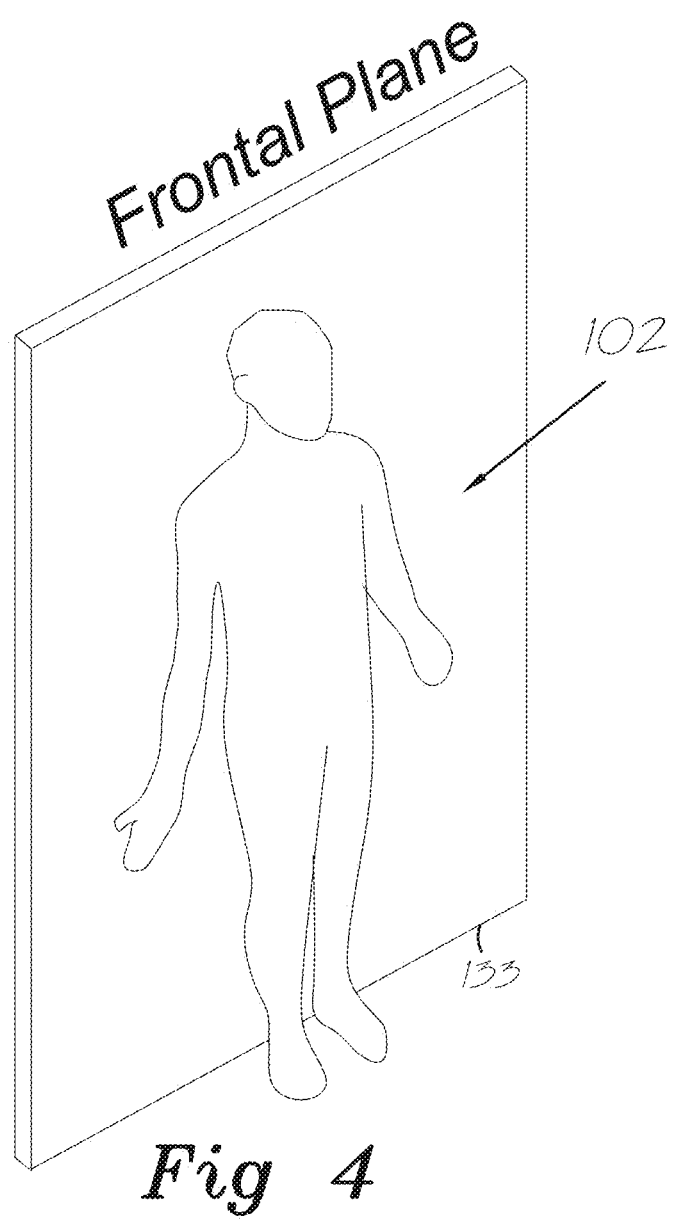
FIG. 4 depicts the frontal plane.

In some embodiments, as shown in FIG. 1, mechanical structures 110 and 112 are coupled to the posterior of mechanical torso 104. FIG. 4 shows a view of person 102. Frontal plane 133, as shown in FIG. 4, separates the space around the person into interior and posterior areas. The posterior of mechanical torso 104 is the part of the mechanical torso which is located behind the person's frontal plane 133. As shown in FIG. 1 and FIG. 3, mechanical structures 110, 112, and 113 are coupled to the posterior of mechanical torso 104.

Figure 5:
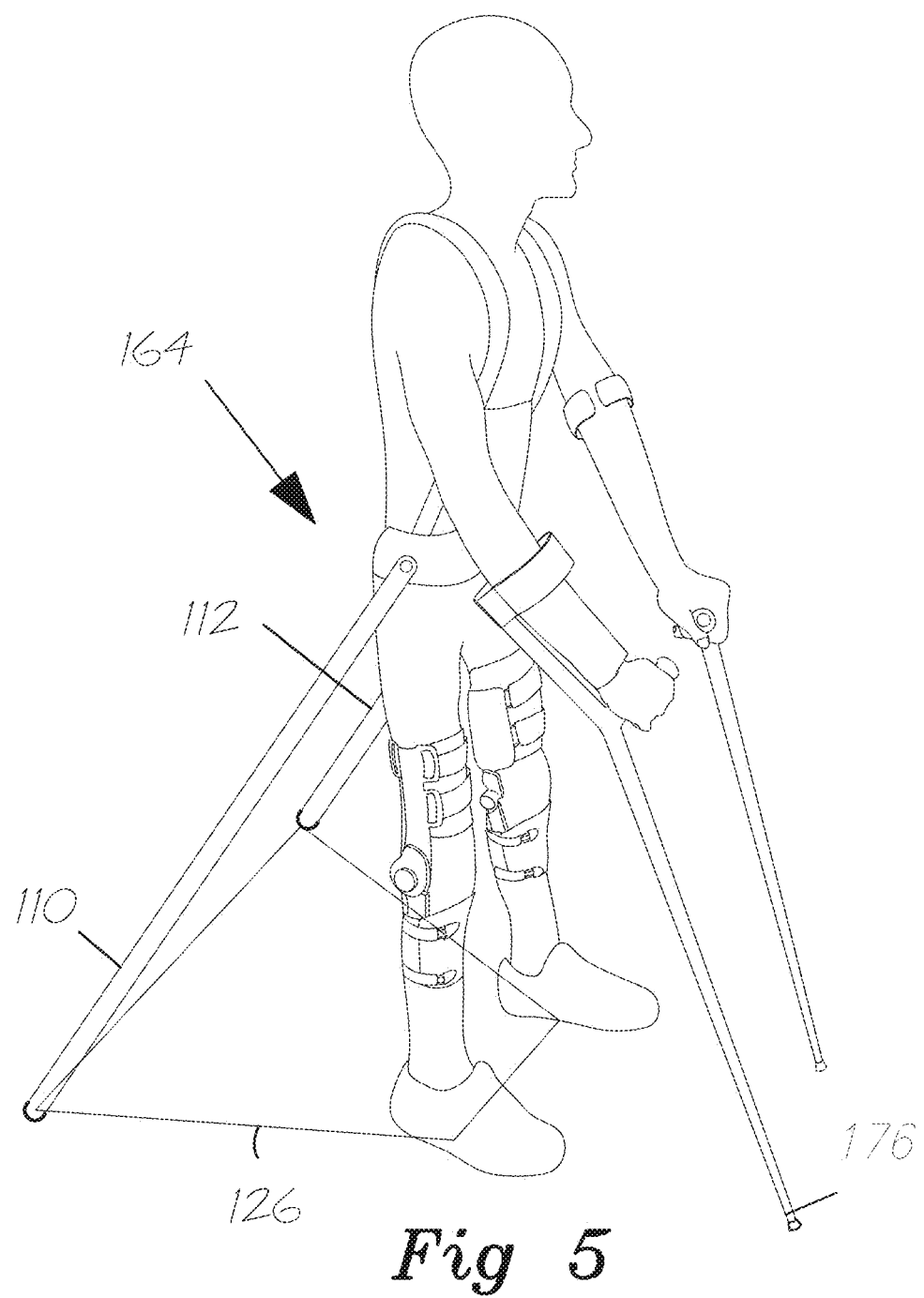
FIG. 5 depicts an embodiment of fall prevention device where the mechanical structures are coupled to the side of mechanical torso.
Figure 6:
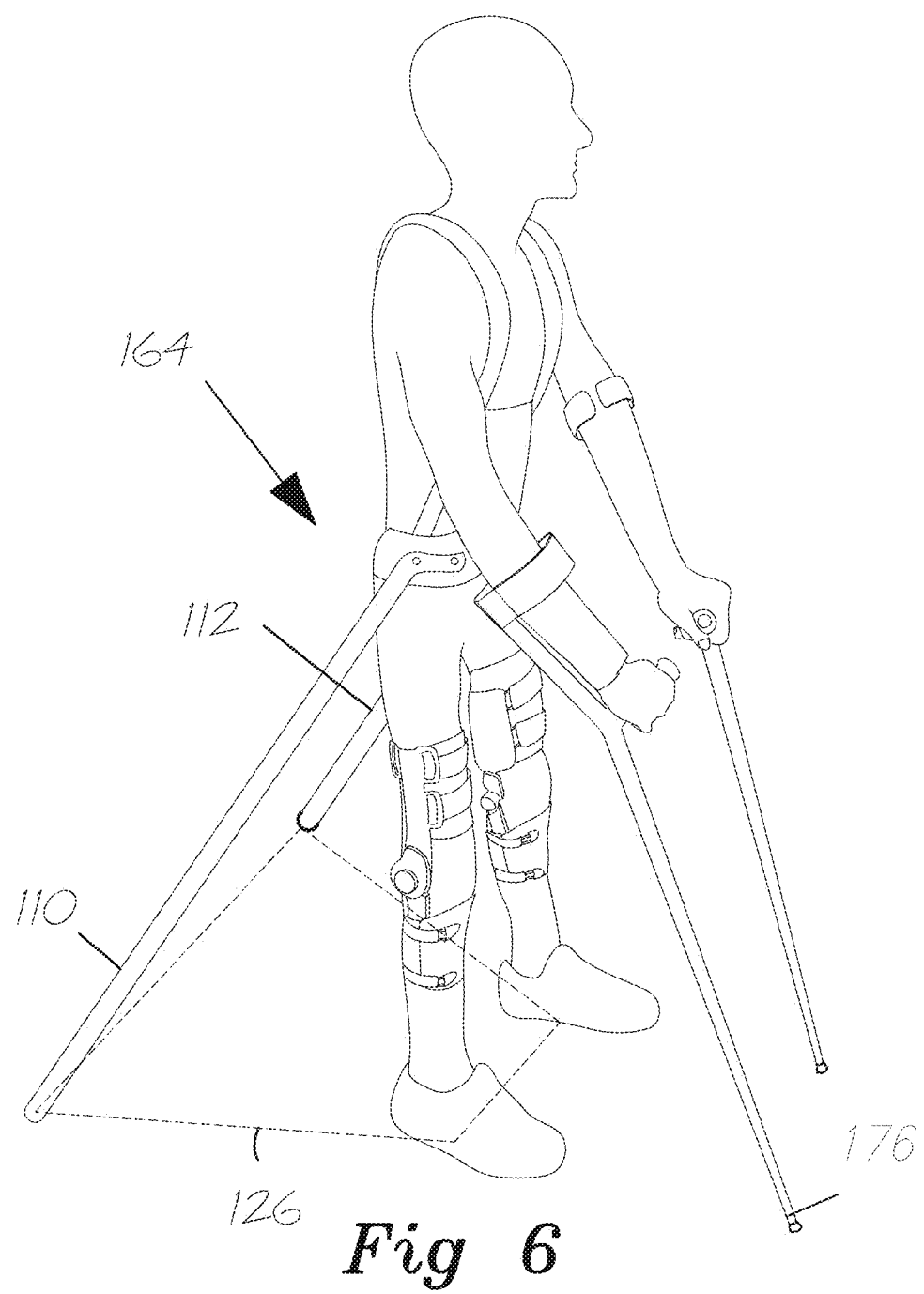
FIG. 6 depicts an embodiment of fall prevention device where the mechanical structures are coupled to the front of mechanical torso.

In some embodiments, as shown in FIG. 5, mechanical structures 110 and 112, are coupled to the side of mechanical torso 104. In some embodiments, as shown in FIG. 6 mechanical structures 110 and 112 are coupled to the front of mechanical torso 104. The front of mechanical torso 104 is the part of the mechanical torso which is located in front of the person 102's frontal plane 133, as shown in FIG. 4. This arrangement allows the user to connect and disconnect mechanical structures 110 and 112 with ease. In both embodiments shown in FIG. 5 and FIG. 6, the second ends 118 and 120 of mechanical structures 110 and 112 contact the ground points behind the person.

Figure 7:
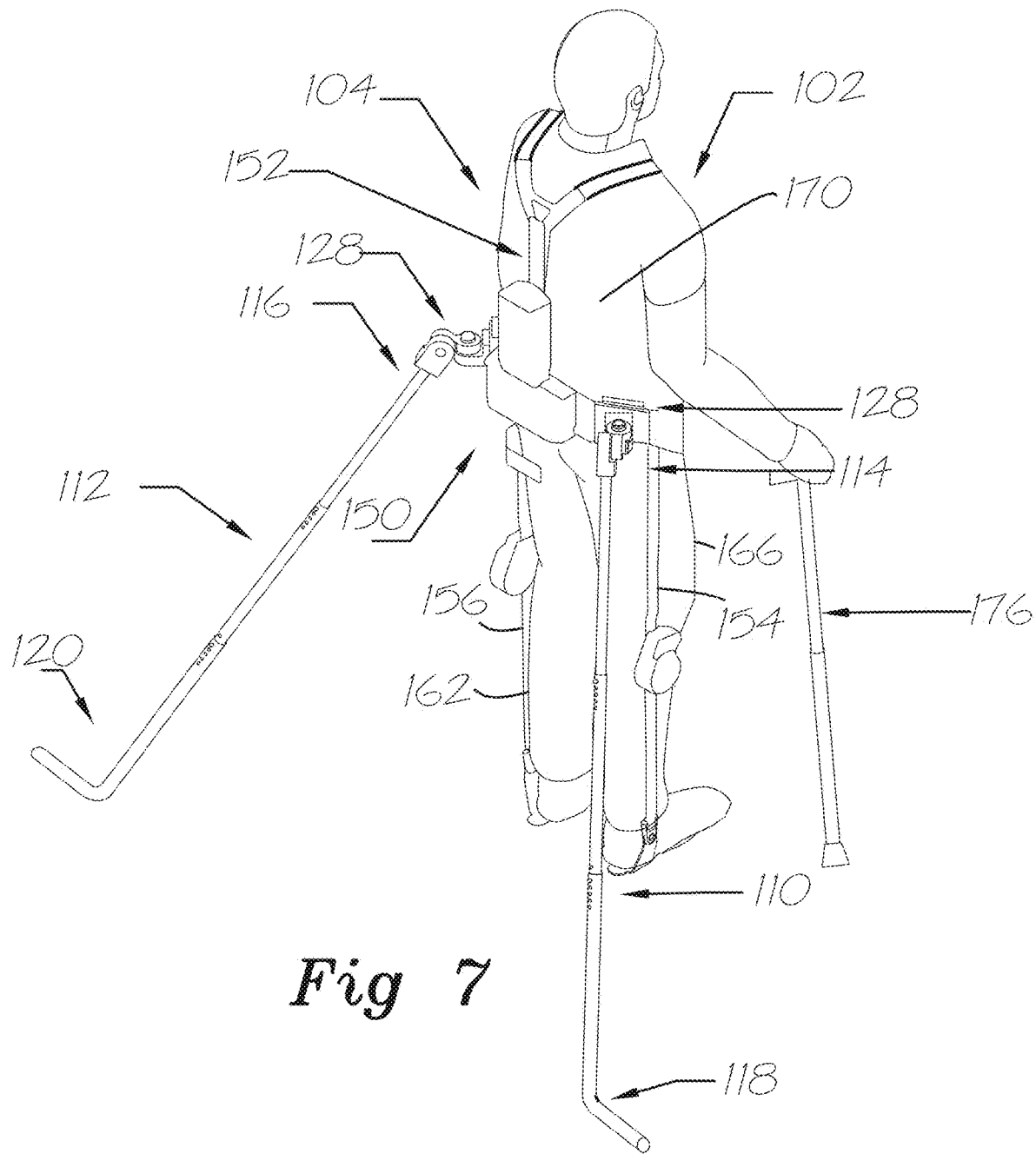
FIG. 7 depicts an embodiment of fall prevention device with mechanical structures that have ends that look like hockey sticks, and where the fall prevention device is coupled to a lower extremely exoskeleton.
Figure 8:
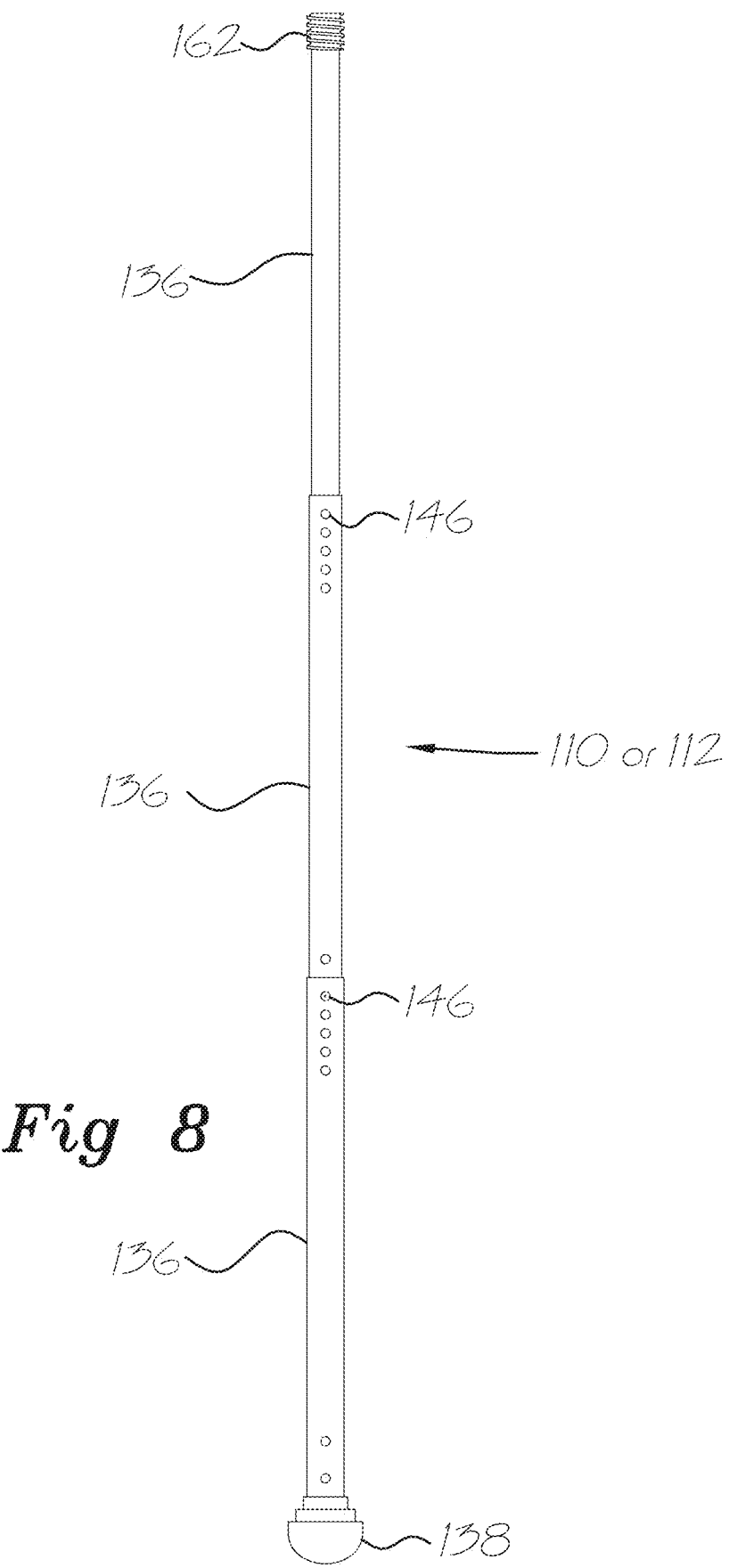
FIG. 8 depicts an embodiment of mechanical structures of the fall prevention device.

In some embodiments, as shown in FIG. 1, each mechanical structure 110 and 112 comprises a pole. An ordinary skilled in the art can consider other forms and shapes for mechanical structures 110 and 112 to provide the intended functions. For example, FIG. 7 shows an embodiment where mechanical structures 110 and 112 look like a hockey stick. FIG. 7 also shows mechanical torso 104 has become a component of the lower extremity exoskeleton 150.

Figure 12:
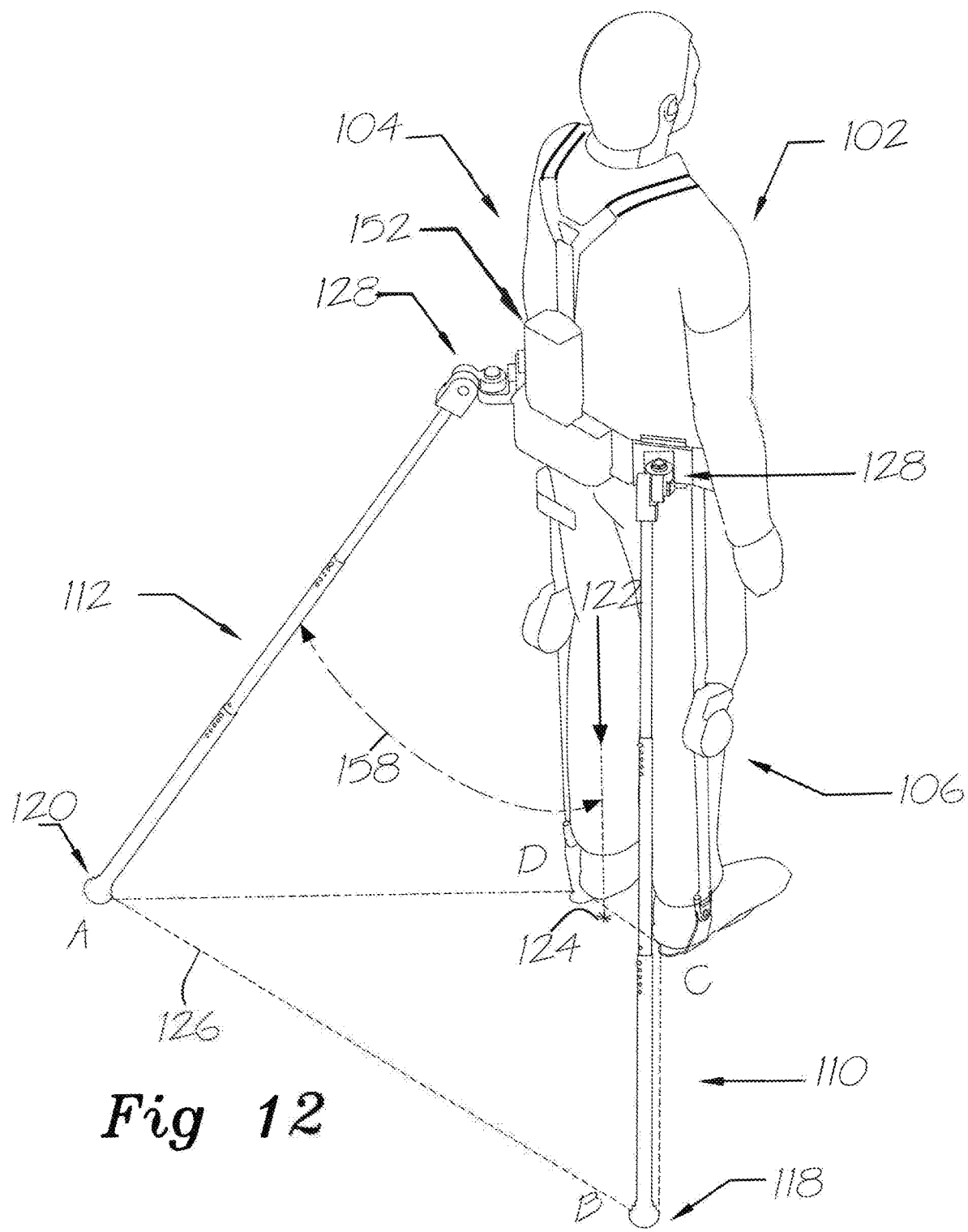
FIG. 12 depicts an embodiment of fall prevention device where angular adjustment mechanism is employed to change the orientation of the mechanical structures, and where the fall prevention device is coupled to a lower extremely exoskeleton.

In some embodiments, mechanical torso 104 is configured to be coupled a lower extremity exoskeleton 150 as shown in FIG. 7 and FIG. 12. Lower extremity exoskeleton 150, among other things, comprises an exoskeleton torso 152 which is configured to be coupled to the person's torso 170. In some embodiments, lower extremity exoskeleton 150 further comprises two exoskeleton legs 154 and 156 which are rotatably coupled to exoskeleton torso 152 and configured to be coupled to the person's legs 162 and 166. This is usually done through thigh braces and shank braces. In some embodiments, mechanical torso 104 is coupled a lower extremity exoskeleton 150. In some embodiments, mechanical torso 104 is coupled to exoskeleton torso 152. In some embodiments, when fall prevention device 164 is coupled a lower extremity exoskeleton 150, mechanical torso 104 of the fall prevention device 164 is the same as exoskeleton torso 152. In some embodiments, prevention device is configurable to be coupled to an exoskeleton through a quick disconnect mechanism. In some embodiments, mechanical structures are 110 and 112 are configurable to be coupled to an exoskeleton through quick disconnect mechanisms.

Figure 9:
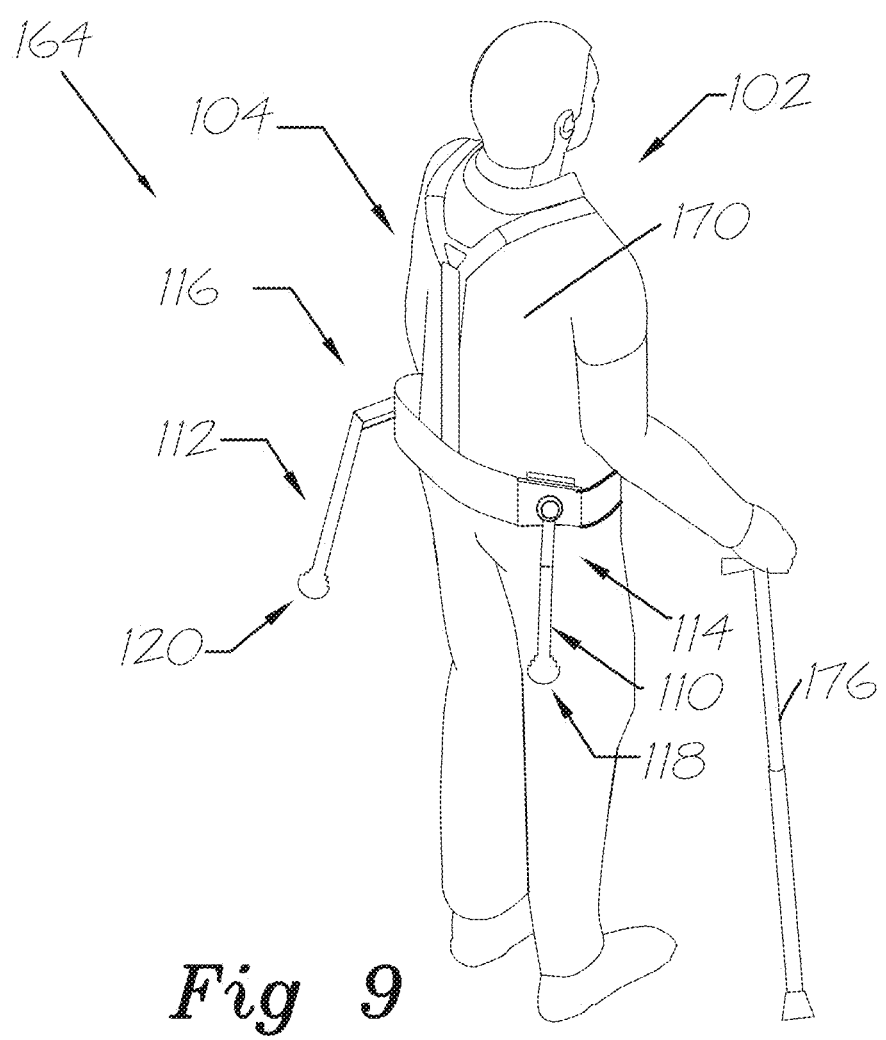
FIG. 9 depicts an embodiment of fall prevention device with the mechanical structures retracted.
Figure 10:
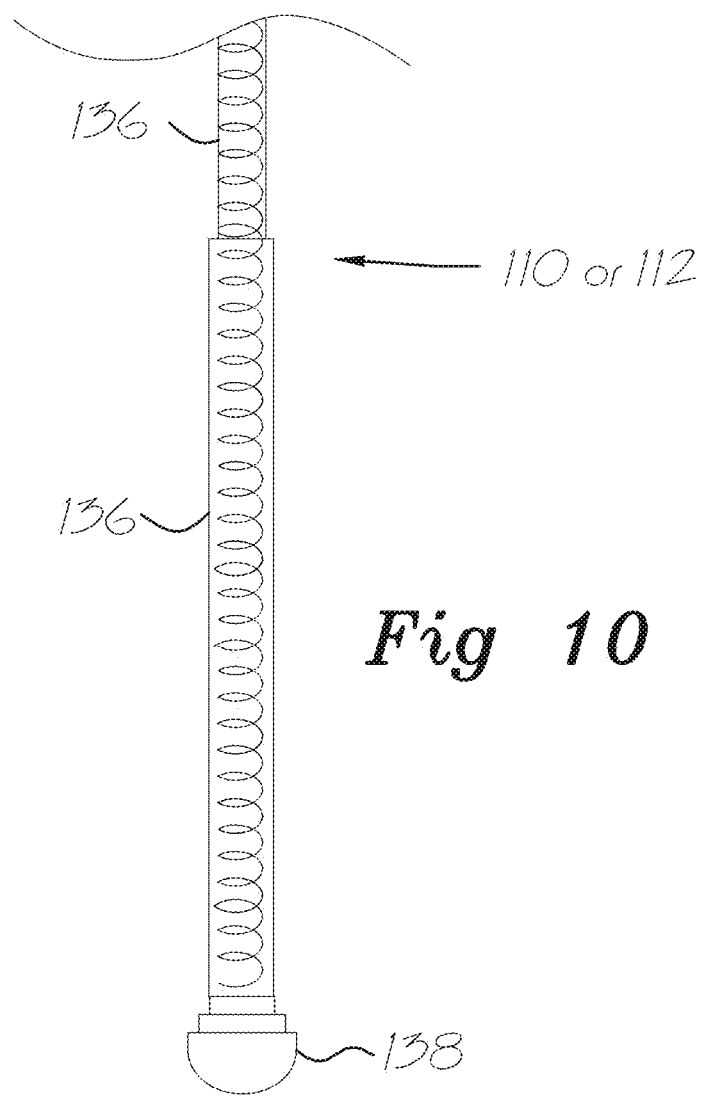
FIG. 10 depicts an embodiment of the spring loaded mechanical structure of fall prevention device.

In some embodiments, as shown in FIG. 7, mechanical structures 110 and 112 are configured to be adjustable in length. In some embodiments, each mechanical structure 110 and 112 comprises one or a plurality of concentric sections (units) 136 configured to slide into one another. FIG. 7 shows an embodiment of mechanical structure 110 or 112 wherein each mechanical structure 110 and 112 comprises one or more of a plurality of tubular sections 136, which may be concentric tubular sections that have tubular cross sections, configured to slide into one another. In some embodiments, as shown in FIG. 7, concentric sections 136 comprise hole pattern 146. Hole pattern 146 is intended to house pins, screws, or other fasteners to secure concentric sections 136 together after adjusting. FIG. 9 shows an embodiment of fall prevention device 164 wherein concentric sections 136 are retracted to yield a shorter length for mechanical structures 110 and 112. In some embodiments, as shown in FIG. 10, concentric sections 136 are spring loaded to promote concentric sections 136 to extend and/or retract effortlessly and quickly. This spring will also help person 102 to move from standing to sitting position slowly and stably when concentric sections 136 retract because they support the person 102's weight. In some embodiments, mechanical structures 110 and 112 are configured to be utilized for posterior support when the person 102 is going from sitting to standing position and vice versa. The posterior support may include providing an external force.

Figure 11:
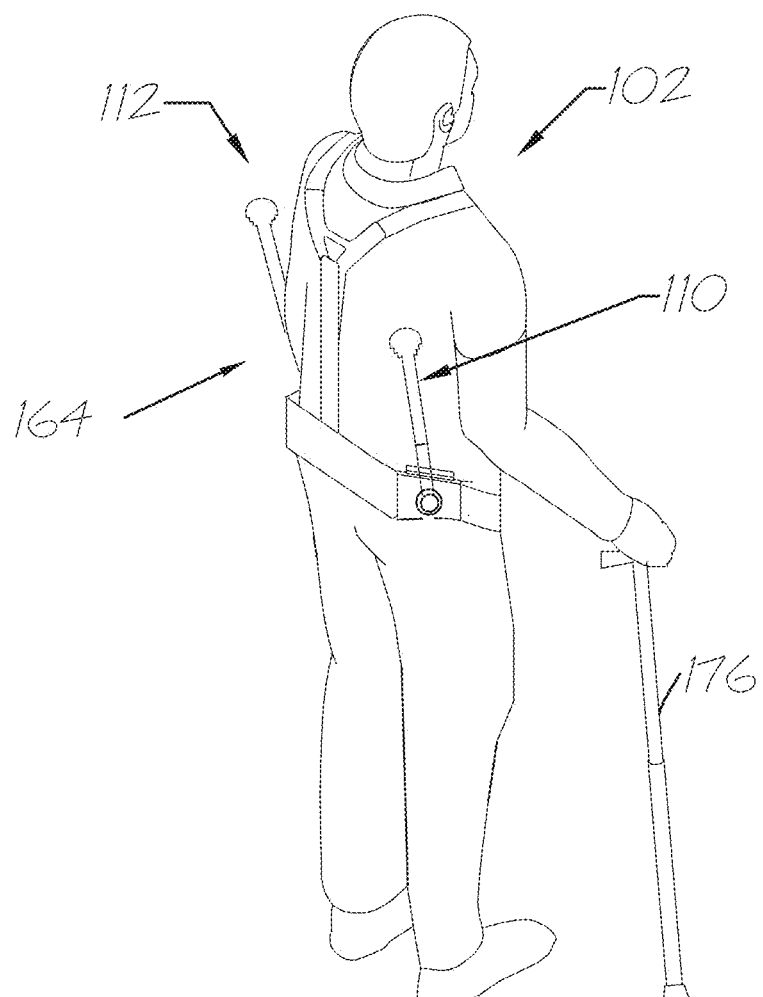
FIG. 11 depicts an embodiment of mechanical structure where they are stored away.

In some embodiments, mechanical structures 110 and 112 can be engaged and retracted, stowed (and/or folded) away when not in use, as shown in FIG. 11.

It can be observed in FIG. 2 and FIG. 3 that, the larger polygon 126 is, the more stability range is provided for person 102. As shown in FIG. 12, when mechanical structure 112 contacts the ground, the line joining the ground contact point of mechanical structure 112 (shown by A) to the coupling location of mechanical structure 112 to mechanical torso 104 makes an angle 158 with vertical gravitational line 122. The same is true for coupling of mechanical structure 110 and mechanical torso 104; the coupling location of mechanical structure 110 and mechanical torso 104 makes an angle 158 with vertical gravitational line 122.

In some embodiments, angle 158 is chosen to be between 12 degrees and 24 degrees. The choice of angle 158 depends on the person 102's height and other parameters. In some embodiments, the angle 158 of the mechanical structures 110 and 112 with respect to the mechanical torso 104 are adjustable. The adjustability of the angle of the mechanical structures 110 and 112 with respect to the mechanical torso 104 allows the user or person 102 to provide a suitable value for angle 158. It is noted that, as stated above, the lengths of mechanical structures 110 and 112 are adjustable in length also. When a locking mechanism is in a first position, the locking mechanism prevents the mechanical structure from adjusting the length of the at least one mechanical structure, and wherein when the locking mechanism is in a second position, the locking mechanism allows the mechanical structure to adjust in length. With the adjustability of mechanical structures 110 and 112, and adjustability of angle 158, one can provide various desirable dimensions for polygon 126.

In some embodiments as shown in FIG. 12, the coupling of mechanical structures 110 and 112 to mechanical torso 104 is adjustable through an adjusting mechanism 128. Adjusting mechanism 128 modifies the angle of the line joining the ground contact point A to the coupling location of mechanical structure 112 to mechanical torso 104. This, in return, modifies the angle 158 of mechanical structure 112 with the vertical gravitational line 122. Similarly, adjusting mechanism 128 modifies the angle 158 of the line joining the ground contact point B to the coupling location of mechanical structure 110 to mechanical torso 104. This, in return, modifies the angle 158 of mechanical structure 110 with the vertical gravitational line 122.

Figure 13:
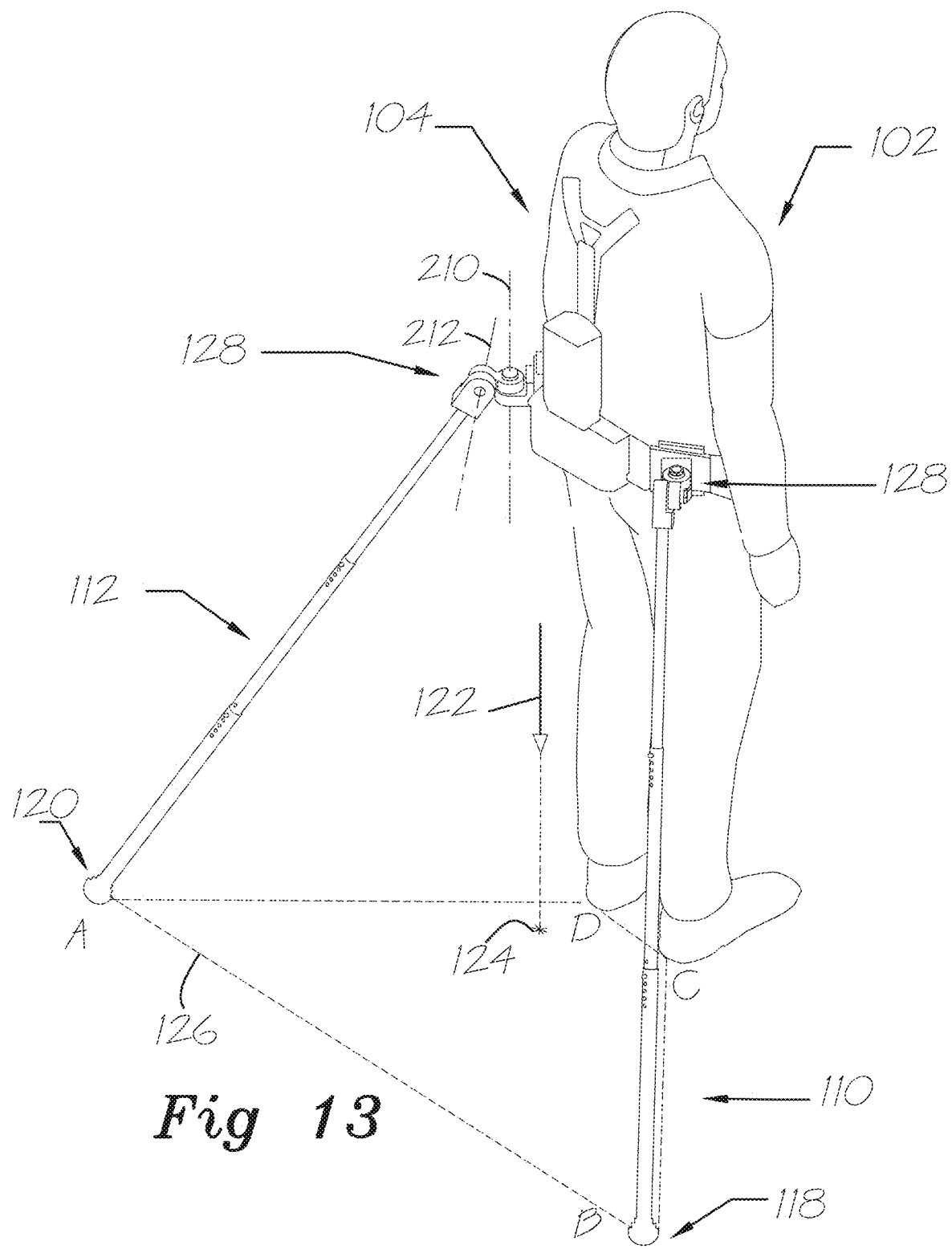
FIG. 13 depicts the adjust axes of the angle adjustment mechanism.
Figure 14:
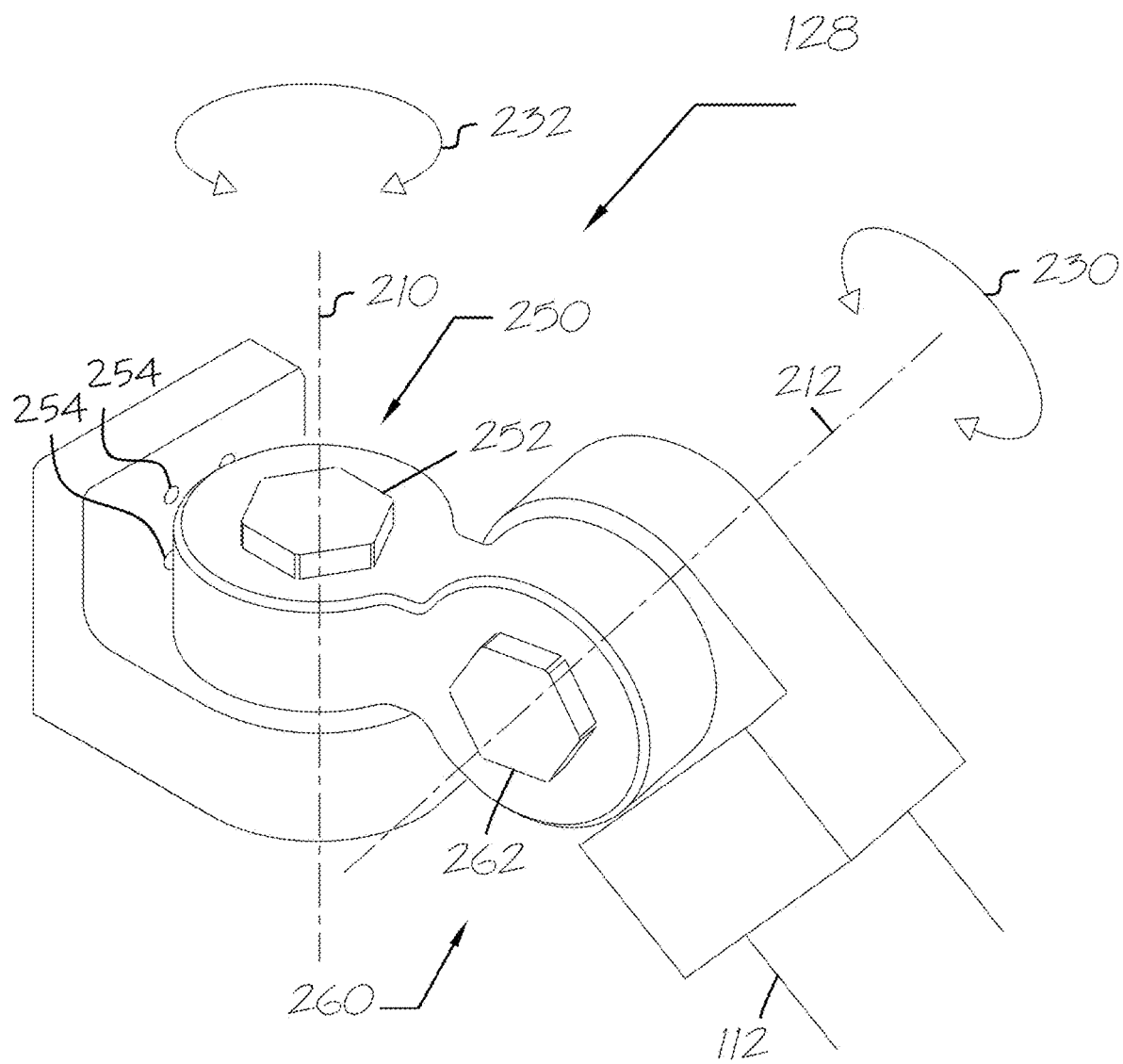
FIG. 14 depicts an embodiment of the angle adjustment mechanism.

In some embodiments, as shown in FIG. 13 and FIG. 14, adjusting mechanism 128 comprises a rotary joint 250 wherein mechanical structure 112 rotates relative to mechanical torso 104 through a rotary joint 250. In some embodiments, rotary joint 250 comprises a rotational axis 210 which is substantially parallel to vertical gravitational line 122. Adjusting mechanism 128 further comprises a locking mechanism which is capable of locking rotary joint 250, preventing the rotation of mechanical structure 112 relative to mechanical torso 104, along axis 210. One of ordinary skilled in the art would appreciate that a variety of locking mechanisms may be utilized to implement locking rotary joint 250. In some embodiments, as shown in FIG. 14, the locking mechanism comprises a fastener 252. In operation, while fastener 252 is not tightened, mechanical structure 112 can rotate along axis 210. Once fastener 252 is tightened, then mechanical structure 112 cannot rotate along axis 210. The rotation along axis 210 allows for changing the orientation of mechanical structure 112 relative to mechanical torso 104. Fasteners 254 are used to couple adjusting mechanism 128 to mechanical torso 104. Adjusting mechanism 128 can also be used with mechanical structure 110 in a similar manner.

In some embodiments, as shown in FIG. 13 and FIG. 14, adjusting mechanism 128 comprises a rotary joint 260, wherein mechanical structure 112 rotates relative to mechanical torso 104 through a rotary joint 260. In some embodiments, rotary joint 260 comprises an axis of rotation, such as axis 212, which is substantially orthogonal to vertical gravitational line 122. Adjusting mechanism 128 further comprises a locking mechanism which is capable of locking rotary joint 260, preventing the rotation of mechanical structure 112 relative to mechanical torso 104 along axis 212. An ordinary skilled in the art would be able to design variety of locking mechanisms to lock rotary joint 260. In some embodiments, as shown in FIG. 14, the locking mechanism comprises a fastener 262. In operation, while fastener 262 is not tightened, mechanical structure 112 can rotate along axis 212. Once fastener 262 is tightened, then mechanical structure 112 cannot rotate along axis 212. The rotation along axis 212 allows for changing the orientation of mechanical structure 112 relative to mechanical torso 104. Adjusting mechanism 128 can also be used with mechanical structure 110 in a similar manner.

Although FIG. 14 shows an adjusting mechanism 128 with two rotary joints, it will be appreciated that other joints may be used. For example, a universal joint may be used to create adjustability between mechanical structures 110 and 112 and mechanical torso 104. In some embodiments, a lockable ball and socket joint can be used to adjust the orientation of mechanical structures 110 and 112 relative to mechanical torso 104. In some embodiments, a universal joint can be used to adjust the orientation of mechanical structures 110 and 112 relative to mechanical torso 104.

Figure 15:
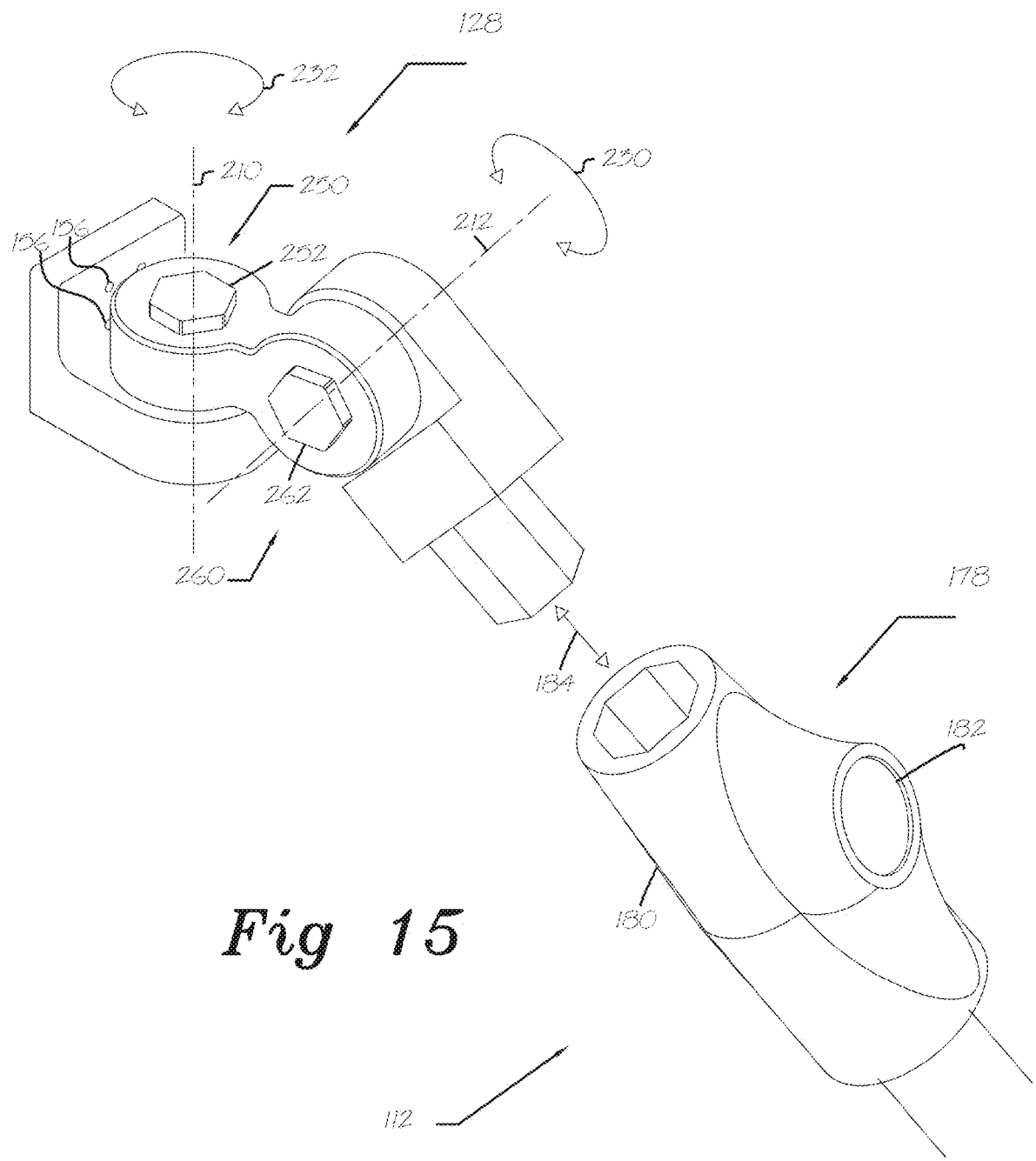
FIG. 15 depicts an embodiment of the locking mechanism of the mechanical structure of the fall prevention device.

In some embodiments, mechanical structures 110 and 112 can be connected and disconnected from mechanical torso 104. This allows ease of transportation, shipping, and storage of fall prevention device 164. In some embodiments, as shown in FIG. 15, fall prevention device 164 further comprises a locking mechanism 178. Locking mechanism 178 allows connecting and disconnecting of mechanical structures 110 and 112 to mechanical torso 104. Locking mechanism 178 comprises at least a first and second positions. In operation, when locking system 178 is in its first position, it prevents mechanical structures 110 and 112 from disconnecting from mechanical torso 104. In its second position, locking mechanism 178 allows mechanical structure 110 or 112 to disconnect from mechanical torso 104. FIG. 15 shows an embodiment of locking system 178. Locking system 178, comprises a button housing 180 and button 182. When button 182 is not pressed, locking system 178 is in its first position and mechanical structure 110 cannot be separated from mechanical torso 104. When button 182 is pressed, locking system 178 is in its second position and mechanical structure 110 can be separated from mechanical torso 104. Arrow 184 in FIG. 15 represents the movement directions of mechanical structures 110 and 112 relative to mechanical torso 104 during connection and disconnection.

Figure 16:
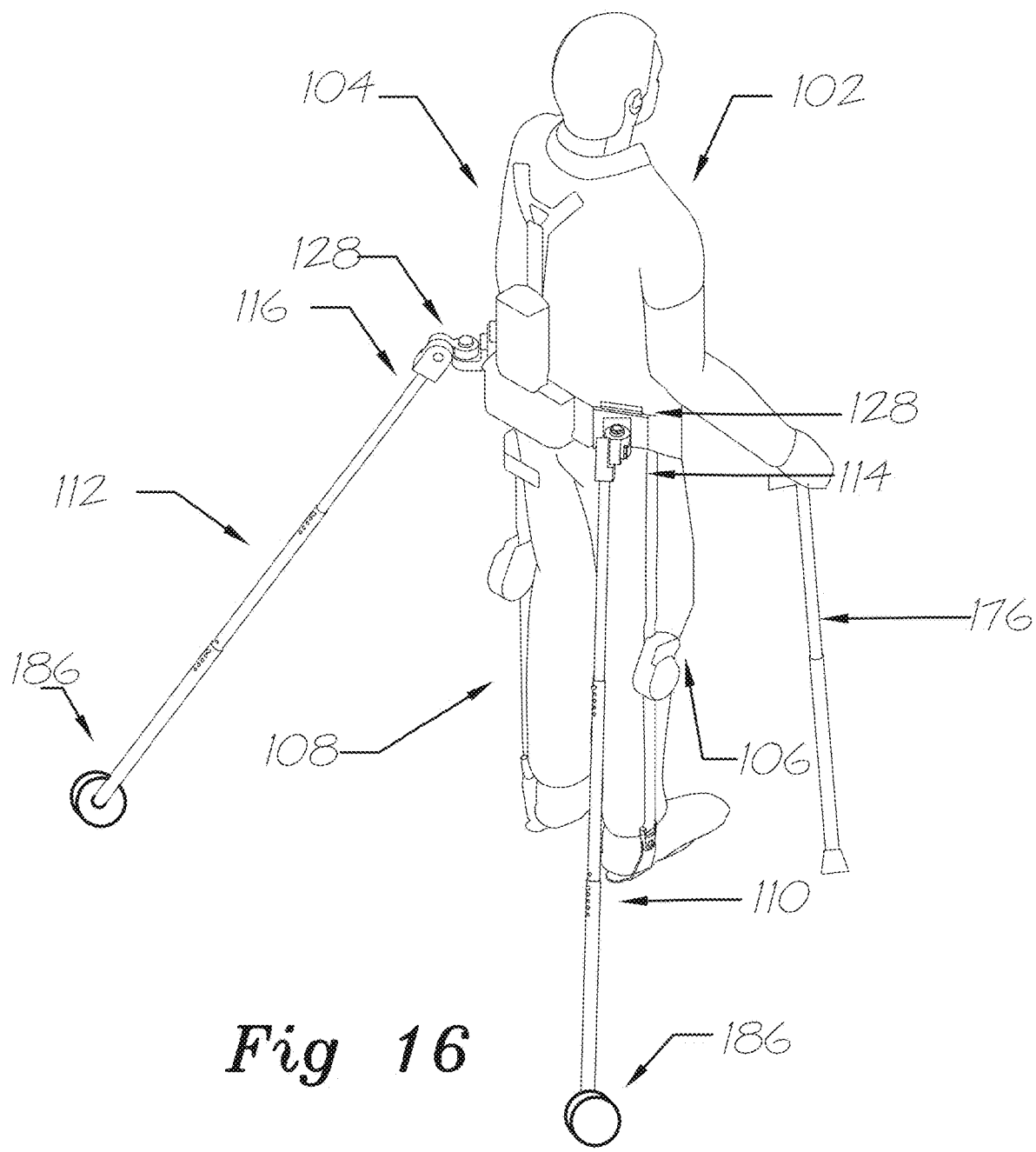
FIG. 16 depicts an embodiment of fall prevention device where the mechanical structures comprises wheel.

As shown in FIG. 16, in some embodiments, mechanical structures 110 and 112 may touch the ground at all times. In this case, one may wish to decrease the amount of drag created by the second ends 118 and 120 of the mechanical structures 110 and 112 on the ground, by adding wheel attachments 186 on the second ends 118 and 120 of the mechanical structures 110 and 112. The wheel attachments 186 can be locked and unlocked to prevent the user from sliding further on the wheels to prevent fall. In some embodiments, wheel attachments 186 can rotate only along one direction when the user or person 102 moves forward.

Figure 17:
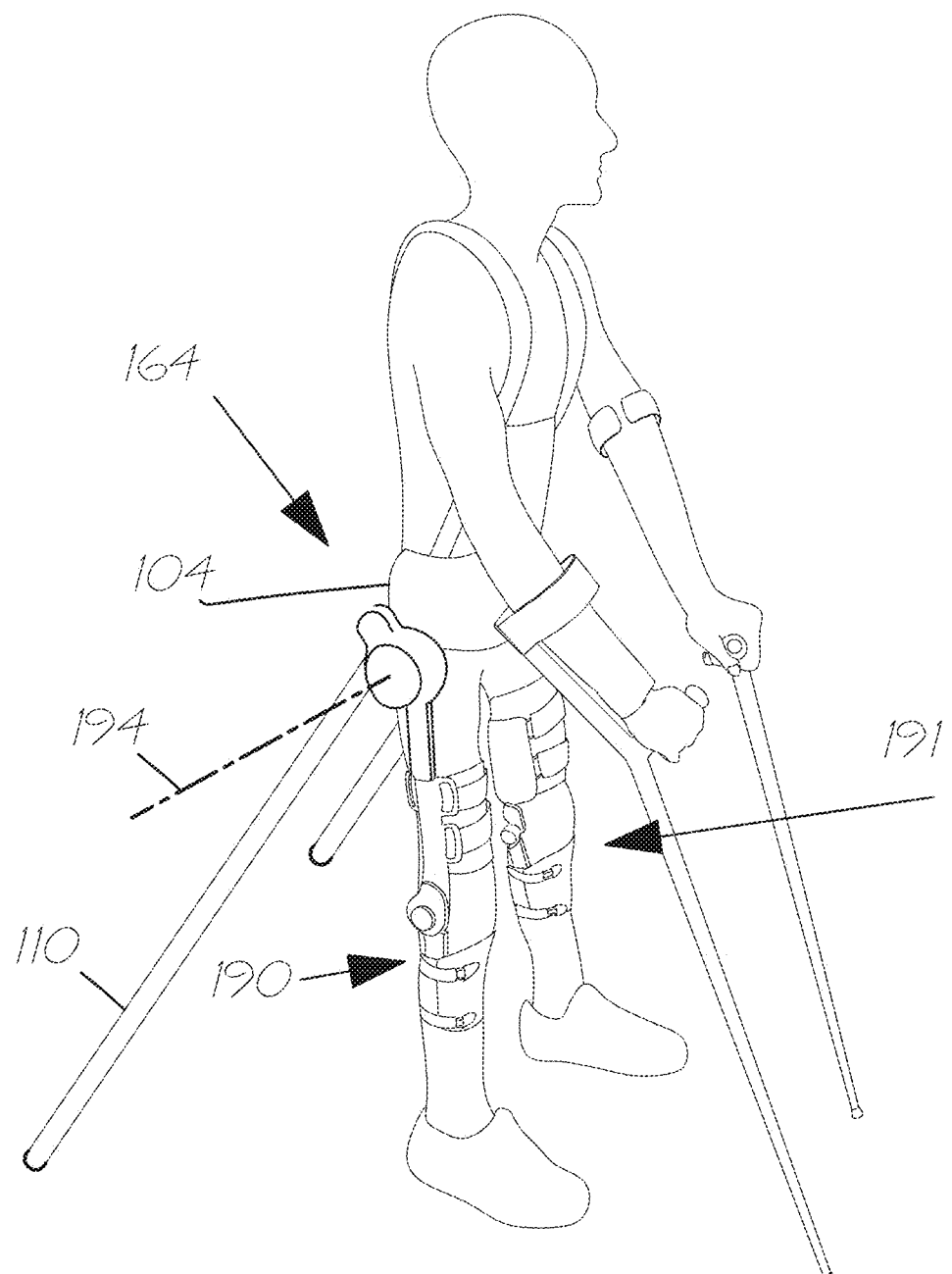
FIG. 17 depicts an isometric view of the fall prevention device comprising two orthotic legs wearable by the person.
Figure 18:
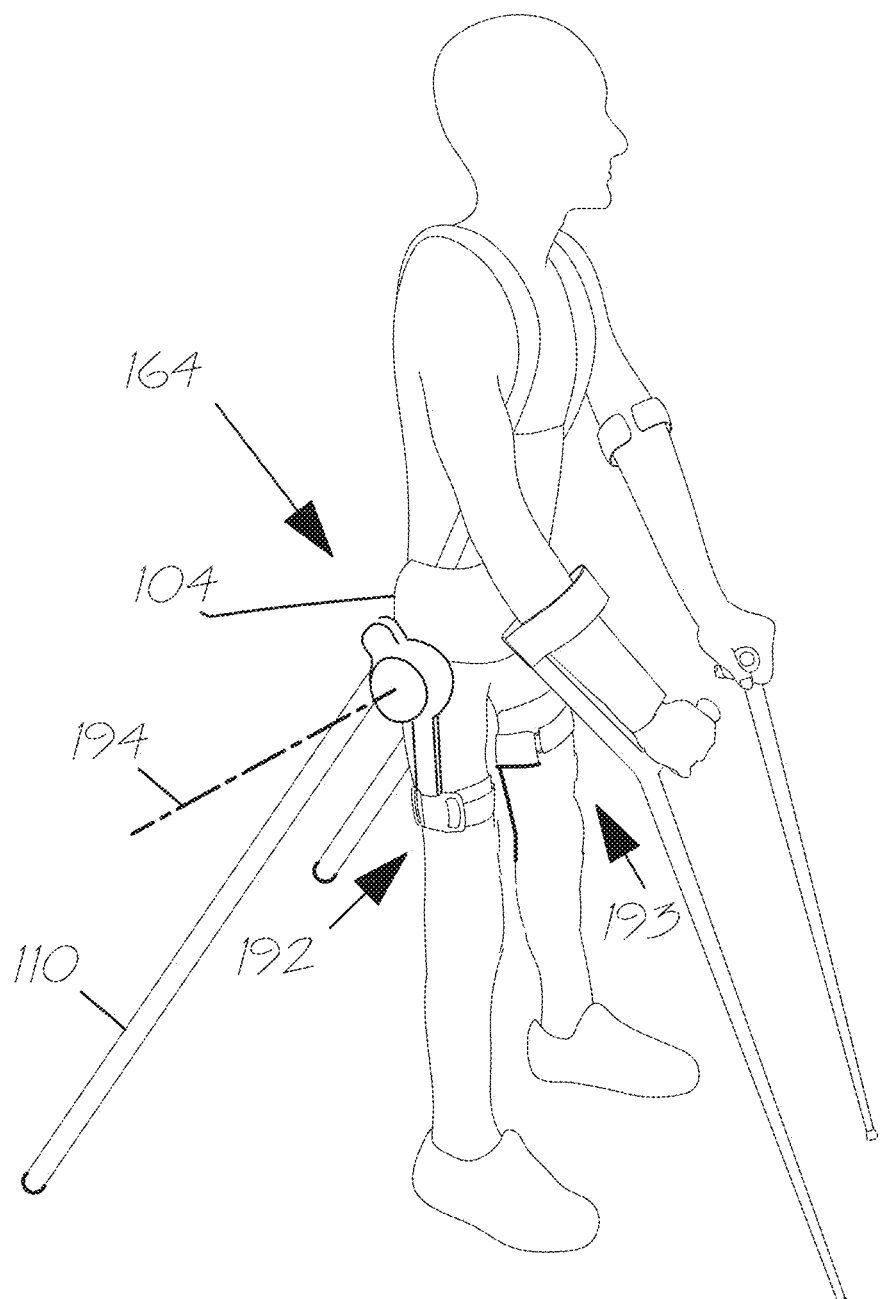
FIG. 18 depicts an isometric view of the fall prevention device comprising two orthotic legs wearable by the person.

Fall prevention device 164 can be used by individuals who wear orthoses and are at the risk of falling. In some embodiments, as shown in FIG. 17, fall prevention device 164 comprises two hip-knee orthotic legs 190 and 191. Hip-knee orthotic legs 190 and 191 are rotatably coupled to mechanical torso 104. Axis 194 shows the rotation of hip-knee-orthotic leg 190 relative to mechanical torso 104. In some embodiments, as shown in FIG. 18, fall prevention device 164 comprises two hip orthotic legs 192 and 193. Hip-orthotic legs 192 and 193 are rotatably coupled to mechanical torso 104. Axis 194 shows the rotation of hip-orthotic leg 192 relative to mechanical torso 104. In some embodiments, similar to embodiments fall prevention device 164 comprises two hip-knee-ankle-foot orthotic legs.

Figure 19:
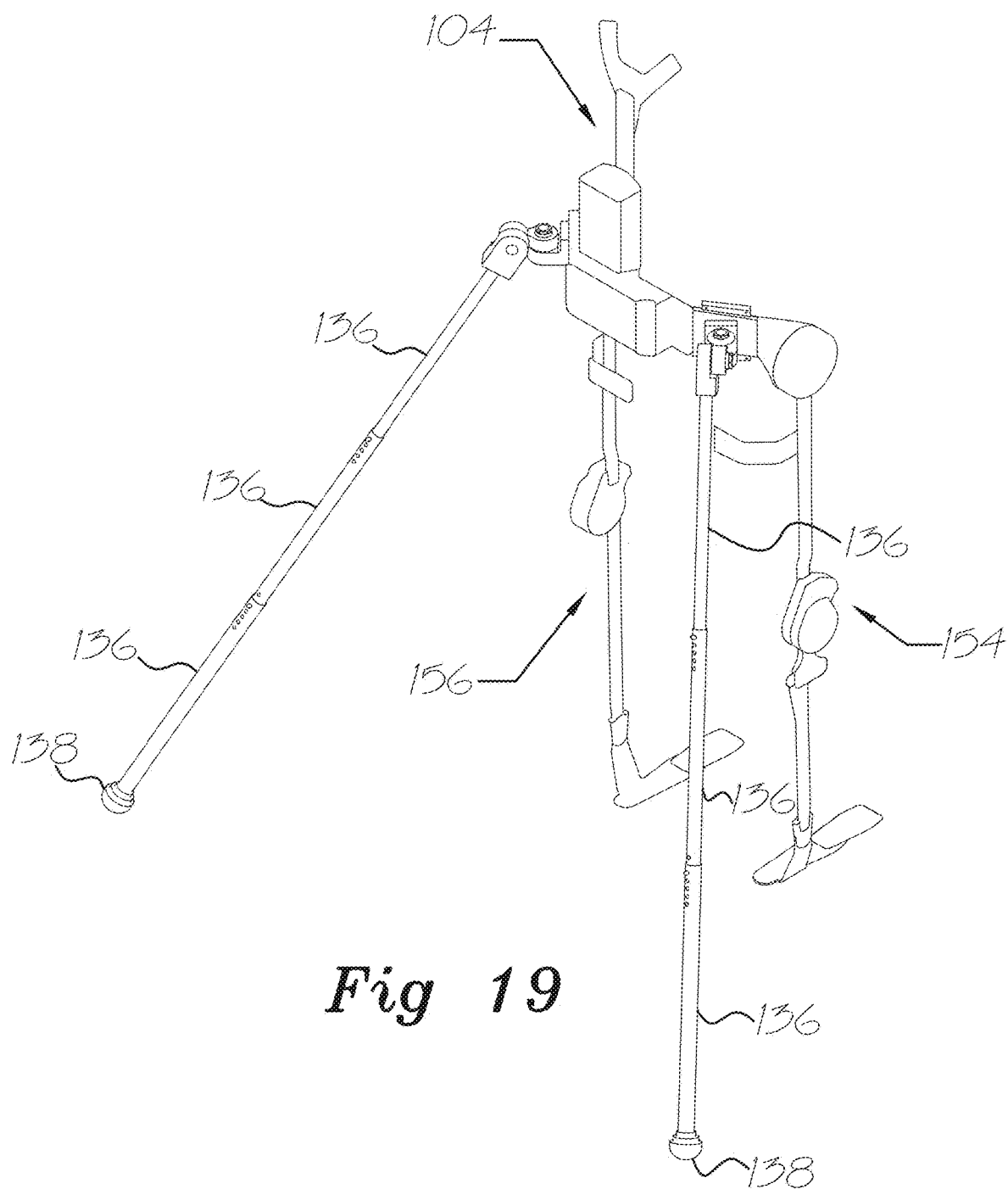
FIG. 19 depicts an embodiment of fall prevention device with mechanical structures having attachments.
Figure 20:
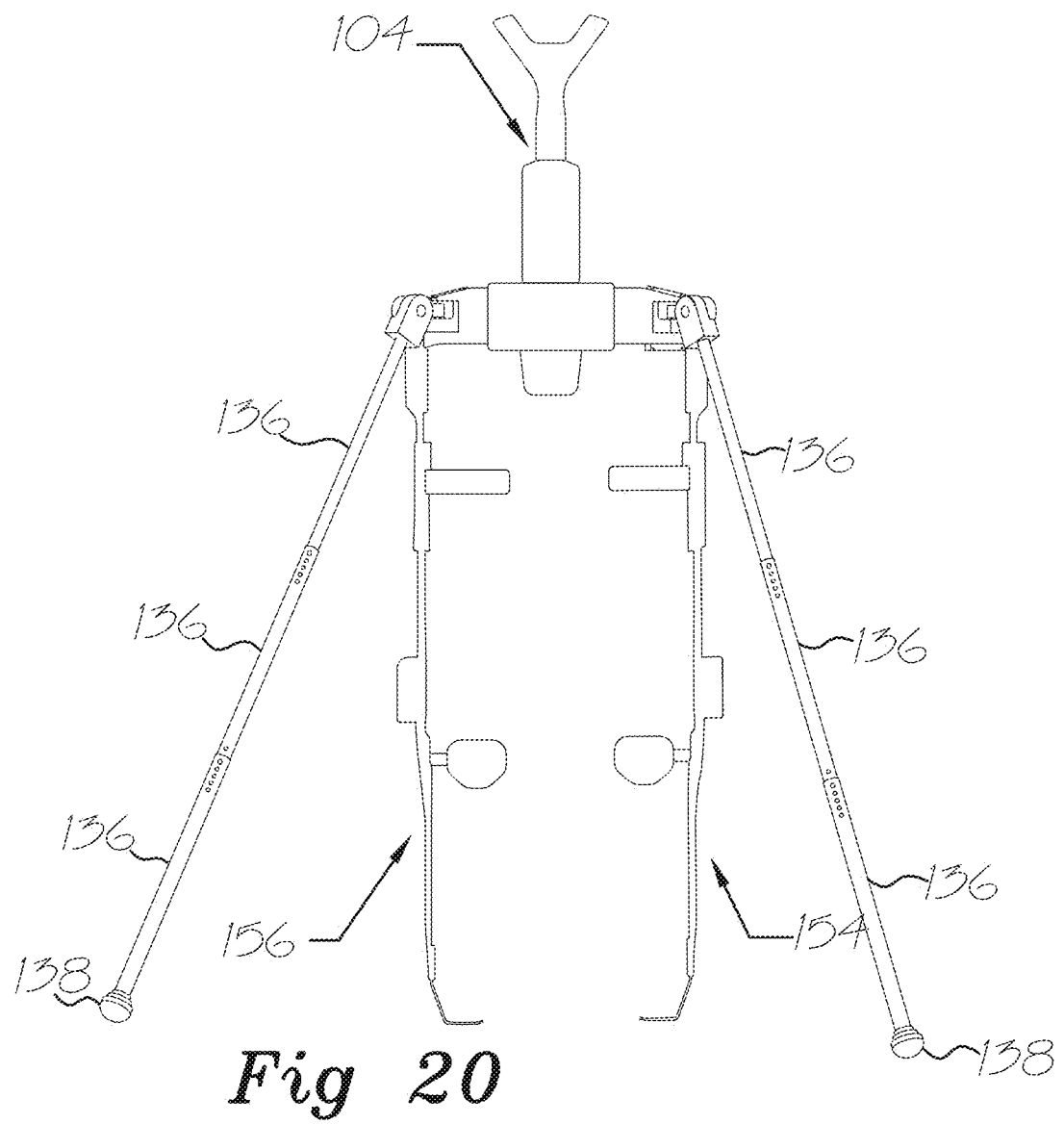
FIG. 20 depicts another view of an embodiment of fall prevention device with mechanical structures having attachments.

FIG. 19 depicts an embodiment of a fall prevention device with mechanical structures having attachments. Accordingly, FIG. 19 provides an additional view of such a fall prevention device that includes mechanical torso 104, as well as exoskeleton legs 154 and 156. In various embodiments, the fall prevention device may also include concentric sections 136 coupled to attachments 138, as discussed above. Moreover, FIG. 20 depicts another view of an embodiment of a fall prevention device with mechanical structures having attachments. As shown in FIG. 20, the fall prevention device may include mechanical torso 104, exoskeleton legs 154 and 156, as well as concentric sections 136 coupled to attachments 138, as discussed above.

While features of the embodiments have been illustrated and described herein, many modifications, changes, and implementations of such features are also contemplated. It is therefore understood that the appended claims are intended to cover all such modifications and changes as fall within the spirit of the embodiments disclosed herein. Moreover, it will be understood that fall prevention device 164 can be coupled to a lower extremity exoskeleton as shown in FIG. 7 and FIG. 12 or can be used without any exoskeleton as shown in FIG. 1 and FIG. 2.

What is claimed is:

1. A fall prevention device configured to be coupled to a person using crutches or a cane, the fall prevention device comprising:
   a mechanical torso configured to be coupled to a torso of the person;
   at least one mechanical structure that is elongated and tubular and comprising a first end and a second end; and
   a rigid coupling to rigidly couple the at least one mechanical structure to the mechanical torso at the first end such that the at least one mechanical structure and the mechanical torso rigidly maintain relative posture to each other, the mechanical torso does not rotate relative to the at least one mechanical structure when coupled to the person, wherein
   the second end of the at least one mechanical structure is configured to be positioned behind the person and close to a ground, such that when the second end of the at least one mechanical structure contacts the ground, contact points of legs of the person on the ground and a contact point of the second end of the at least one mechanical structure on the ground outline a multi-sided polygon on the ground, when a vertical projection of a center of gravity of the person to the ground is configured to intersect the ground within the multi-sided polygon, the fall prevention device is configured to prevent the person from falling backwards or sideways, and the crutches or cane are configured to prevent the person from falling forward.

2. The fall prevention device of claim 1, wherein when the at least one mechanical structure contacts the ground, a line joining the ground contact point of the at least one mechanical structure to a coupling location of the at least one mechanical structure to the mechanical torso makes an angle with the vertical projection such that the ground contact point of the at least one mechanical structure is located behind a frontal plane.

3. The fall prevention device of claim 2, wherein coupling of the at least one mechanical structure to the mechanical torso is adjustable through an adjusting mechanism, and wherein the adjusting mechanism modifies the angle of the line joining the ground contact point to the coupling location of the at least one mechanical structure to the mechanical torso with the vertical projection.

4. The fall prevention device of claim 3, wherein the adjusting mechanism comprises:

at least one rotary joint, wherein the at least one mechanical structure rotates relative to the mechanical torso through the at least one rotary joint; and a locking mechanism configured to lock the rotary joint thereby preventing a rotation of the at least one mechanical structure relative to the mechanical torso during operation.

5. The fall prevention device of claim 1, wherein the at least one mechanical structure comprises one or more of a plurality of concentric units configured to slide into one another.

6. The fall prevention device of claim 5, wherein each of the plurality of concentric units has a tubular cross-section.

7. The fall prevention device of claim 5, wherein the plurality of concentric units is configured to retract.

8. The fall prevention device of claim 1 further comprising a locking mechanism capable of coupling and uncoupling the at least one mechanical structure to and from the mechanical torso.

9. The fall prevention device of claim 8, wherein the locking mechanism comprises at least a first position and a second position, wherein when the locking mechanism is in the first position, the locking mechanism prevents the at least one mechanical structure from uncoupling from the mechanical torso, and wherein when the locking mechanism is in the second position, the locking mechanism allows the at least one mechanical structure to uncouple from the mechanical torso.

10. The fall prevention device of claim 9, wherein when the locking mechanism is in the first position, the locking mechanism prevents the mechanical structure from adjusting a length of the at least one mechanical structure, and wherein when the locking mechanism is in the second position, the locking mechanism allows the mechanical structure to adjust the length of the at least one mechanical structure.

11. The fall prevention device of claim 1, further comprising at least one orthosis rotatably coupled to the mechanical torso.

12. The fall prevention device of claim 11, where the at least one orthosis is a hip-knee-ankle-foot orthosis.

13. The fall prevention device of claim 11, where the at least one orthosis is a hip-knee orthosis.

14. The fall prevention device of claim 1, wherein the second end of the at least one mechanical structure comprises a wheel attachment.

15. The fall prevention device of claim 14, wherein rotation of the wheel attachment is configured to be locked and unlocked.

16. The fall prevention device of claim 1, wherein the mechanical torso is configured to be coupled to a lower extremity exoskeleton, the lower extremity exoskeleton comprising:

an exoskeleton torso configured to be coupled to the torso of the person; and two exoskeleton legs rotatably coupled to the exoskeleton torso and configured to be coupled to legs of the person.

17. The fall prevention device of claim 16, wherein the two exoskeleton legs of the lower extremity exoskeleton are rotatably coupled to the exoskeleton torso.

18. The fall prevention device of claim 1, wherein the at least one mechanical structure is coupled to a posterior of the mechanical torso, and wherein the posterior of the mechanical torso is a part of the mechanical torso which is configured to be located behind a frontal plane of the person.

19. The fall prevention device of claim 1, wherein the at least one mechanical structure comprises a pole.

20. The fall prevention device of claim 1, wherein the mechanical torso comprises a belt configured to be coupled to the person.

21. The fall prevention device of claim 1, wherein the mechanical torso further comprises at least a shoulder strap configured to be coupled to the person.

22. The fall prevention device of claim 1, wherein the at least one mechanical structure is adjustable in length.

23. The fall prevention device of claim 1, wherein an angle of the at least one mechanical structure with respect to the vertical projection is adjustable.

24. The fall prevention device of claim 1, wherein the at least one mechanical structure is configured to fold when not in use.

25. The fall prevention device of claim 1, wherein the at least one mechanical structure is configured to stow away when not in use.

26. The fall prevention device of claim 1 further comprising two lower extremity exoskeleton legs configured to be coupled to the legs of the person.

27. The fall prevention device of claim 1, wherein the at least one mechanical structure is coupled to a side of the mechanical torso.

28. The fall prevention device of claim 1, wherein the at least one mechanical structure is coupled to a front of the mechanical torso, and wherein the front of the mechanical torso is configured to be a part of the mechanical torso located in a front of a frontal plane of the person.

29. The fall prevention device of claim 1, wherein the second end of the at least one mechanical structure comprises an attachment adding traction to the ground.

\* \* \* \* \*